United States Patent [19]

Colburn et al.

[11] 4,353,375

[45] Oct. 12, 1982

[54] ACTIVITY MONITOR FOR AMBULATORY SUBJECTS

[75] Inventors: Theodore R. Colburn, Rockville; Bruce M. Smith, Bethesda, both of Md.

[73] Assignee: The United States of America as represented by the Department of Health & Human Services, Washington, D.C.

[21] Appl. No.: 790,988

[22] Filed: Apr. 26, 1977

[51] Int. Cl.³ .............................................. A61B 5/10
[52] U.S. Cl. .................................................. 128/782
[58] Field of Search .......... 128/2 S, 2 N, 2 R, 2.05 P, 128/2.05 T, 2.06 A, 782; 35/22 R; 340/279

[56] References Cited

U.S. PATENT DOCUMENTS

| | | | |
|---|---|---|---|
| 3,107,664 | 10/1963 | Smith | 128/2.05 P |
| 3,693,590 | 9/1972 | Bowers | 128/25 X |
| 3,807,388 | 4/1974 | Orr et al. | 128/2.05 T X |
| 4,112,926 | 9/1978 | Schulman et al. | 128/2 S |
| 4,117,834 | 10/1978 | McPartland et al. | 128/2 S |

FOREIGN PATENT DOCUMENTS 1383594  2/1975  United Kingdom ................ 128/2 S

OTHER PUBLICATIONS

McPartland et al., "Activity Sensors . . . Evaluation", IEEE Trans. on Bio. Med. Eng., Mar., 1976, pp. 175-178.
McPartland et al., "The Movement Activated . . . ", Behavior Res. Meth. & Inst., 1976, vol. 8 (4), pp. 357-360.
Colburn et al., "An Ambulatory Activity Monitor . . . ", ISA Trans., vol. 15, No. 2, pp. 149-154, May 3, 1976.
Polhemus et al., "A Rocking Motion Sensor . . . ", ISA Trans., vol. 15, No. 2, pp. 192-196, May 3, 1976.

*Primary Examiner*—Lee S. Cohen
*Attorney, Agent, or Firm*—Thomas J. Byrnes; Thomas J. Scott, Jr.; Stanley C. Spooner

[57] ABSTRACT

Disclosed is a monitor apparatus which can be worn by a patient and will provide an indication of activity levels over a number of subsequent time periods. A transducer which is energized by the ambulatory subject's movement, provides an activity pulse into a temporary memory. At the end of a standard timing interval, for example fifteen (15) minutes, a digital code word representative of the total number of activity pulses in that standard timing interval is fed into a solid state memory. The temporary memory is then reset and counts the activity pulses over the next standard timing interval. In this manner, activity levels for any number of sequential time intervals can be recorded without hindering the patient's movement. A contol logic circuit, which is externally triggered, causes the permanent memory to sequentially readout the activity levels of subsequent standard timing intervals for use in studying the activity levels of ambulatory subjects.

20 Claims, 7 Drawing Figures

ACTIVITY MONITOR FOR AMBULATORY SUBJECTS

BACKGROUND OF THE INVENTION

The present invention relates to the measurement of activity levels in human beings.

The measurement of the activity of human subjects is an essential quantification in behavioral research. Movement disorders such as Parkinson's disease and Huntington's chorea, hyperactivity in children, manic depressive illness, and other afflictions are all characterized by abnormal activity. Treatment many times involves the application of various drugs to subjects in an attempt to modify their behavioral activity patterns. One determination of the effectiveness of a particular drug treatment program is the ultimate affect on the individual's activity levels over a long period of time, twenty four hours or greater.

In the manic depressive illness, for example, a long depression is often followed by a rapid but brief return to the normal state, which in turn is followed by the sudden onset of manic behavior. The change from one state to another is called the "switch process" and is a very important research area. It is essential to have accurate activity data in order to show precisely when the switch occurs and to detail how drastic the change in behavioral activity is.

Many prior art methods have been employed to measure activity levels, including devices utilizing capacitive, ultrasonic and telemetric techniques. Each of these methods has advantages and disadvantages but they all require the subject to remain in a particular area. Devices which allowed the patient to move beyond a restricted area generally only provided indications of total physical activity and required numerous readings by trained personnel in order to get a reasonable timebase upon which activity levels can be projected. Furthermore, there are indications that even ward nurses in a retention facility were not positive as to the detecting of a difference in a subject's general activity level. Therefore, even if it were possible to have a subject under observation at all times, there would be no way of ensuring that the time the "switch" process occurs would be accurately recorded. Furthermore, it is extremely difficult through mere observation to determine quantitatively the violence or strength of a particular movement.

SUMMARY OF THE INVENTION

It is, therefore, an object of the present invention to provide a method and apparatus for measuring and recording activity levels over a plurality of consecutive time periods.

It is a further object of the present invention to provide a small, compact activity level monitor capable of recording activity levels in a human patient over a number of time intervals.

A still further object of the present invention is to provide an activity level monitor which is totally self-contained and requires no external input in order to record total activity levels in consecutive time intervals.

The above and other objects are achieved by providing a transducer and amplifier mounted in a small container which is attached to the subject's limb. The transducer supplies a signal to the amplifier when the case (and the limb to which it is attached) is moved. The amplifier increases the signal and, if high enough, provides an output pulse which is considered one activity count. This output pulse is conducted to an event counter which sums all activity counts. A timer supplies a signal which is indicative of the end of the time period in which activity pulses are to be summed. This standard timing interval pulse is transmitted to the event counter which, after providing to the addressable memory a digital word which is indicative of the total activity counts in the standard timing interval, is reset to zero and begins summing the activity counts for the next standard timing interval. An addressable memory stores the digital code words in different locations such that the information can later be read out in a sequential manner. Control logic is incorporated in the system which maintains the appropriate sequence of information set into the addressable memory and controls the readout of the memory when information is extracted therefrom.

BRIEF DESCRIPTION OF THE DRAWINGS

A more complete appreciation of the invention, and many of the attendant advantages thereof, will be readily apparent by reference to the detailed description when considered in connection with the accompanying drawings wherein.

DETAILED DESCRIPTION OF A PREFERRED EMBODIMENT

Figure 1:
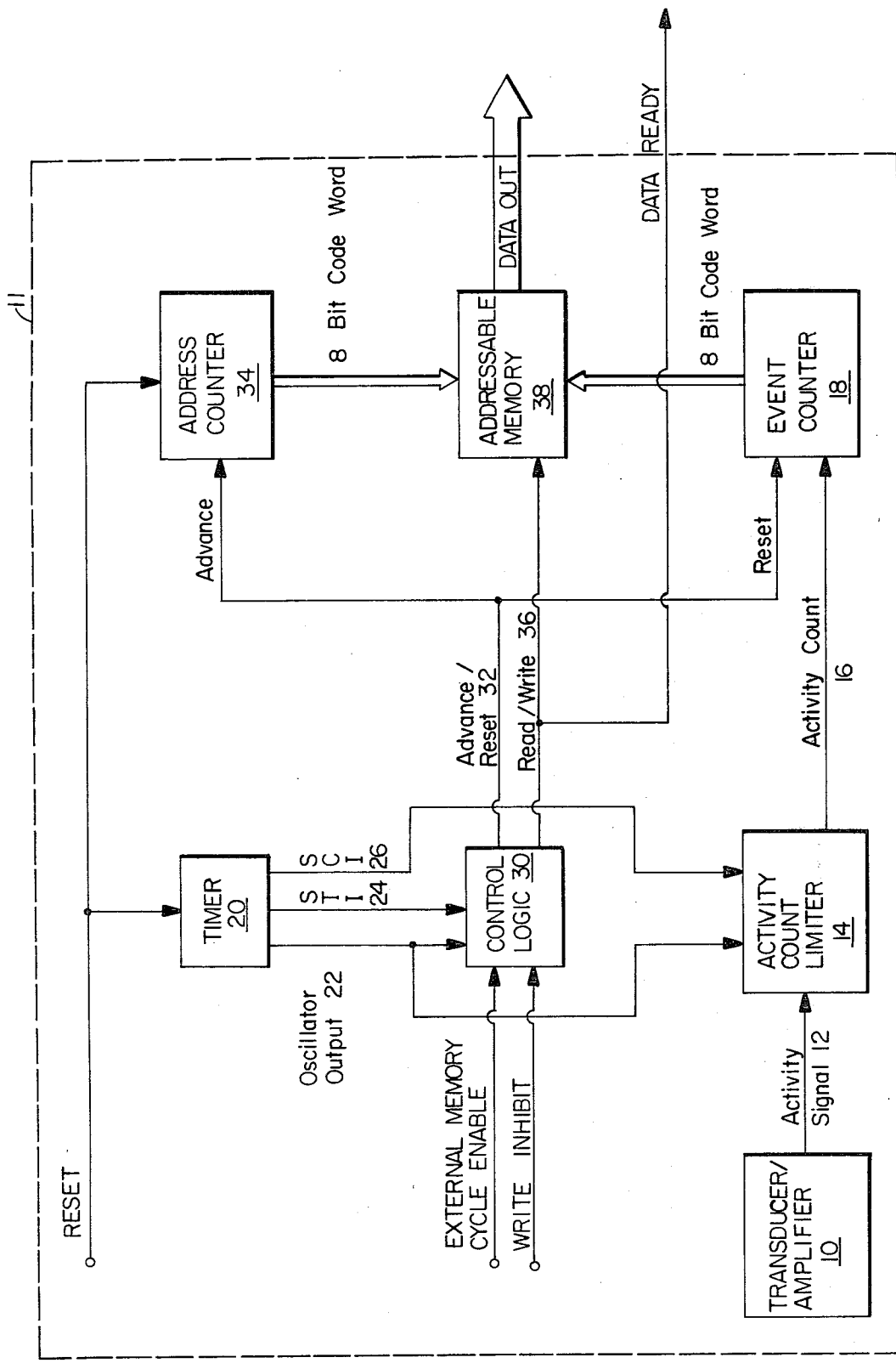
FIG. 1 is an overall block diagram of the activity monitor indicating the flow of information.

Referring now more particularly to the drawings wherein like numerals designate similar parts throughout the several views, and more particularly to FIG. 1, there is shown the basic block diagram of the self-contained activity monitor. The RESET, EXTERNAL MEMORY CYCLE ENABLE, and WRITE INHIBIT inputs to the activity monitor are supplied when the monitor is connected to a readout device. Similarly, the DATA OUT and DATA READY signals are supplied to the readout device. The activity monitor in case 11 indicated by dotted lines can be attached by straps, bandages, etc. to the subject whose activity level will be monitored. The Transducer/Amplifier 10 supplies an Activity Signal 12 which is indicative of the movement level of the limb to which the activity monitor is attached. The activity signal is supplied to an Activity Count Limiter 14. The Limiter 14 provides a fixed level Activity Count 16 when the Activity Signal 12 is above a predetermined threshold level. This activity count is conveyed to the Event Counter 18 which sums the activity counts supplied thereto. A Timer 20 supplies an Oscillator Output 22, a Standard Time Interval 24

(STI), and a Single Count Interval 26 (SCI). Oscillator Output 22 and STI 24 are supplied to Control Logic 30. An Advance/Reset Signal 32 is supplied to Address Counter 34 and Event Counter 18. Additionally, a Read/Write Signal 36 is supplied to the Addressable Memory 38. The Advance/Reset Signal 32 which is applied to Event Counter 18 causes the Counter to return to zero after application of the signal. Immediately before the Advance/Reset Signal 32 is applied, the Read/Write Signal 36 is applied to the Addressable Memory 38 causing it to read and store an 8 Bit Code Word from the Event Counter 18 which is representative of the total number of Activity Counts 16 contained in the Event Counter. After this information is stored in the Addressable Memory 38 the Reset Signal 32 causes the Even Counter to Reset itself to zero and begin summing the Activity Counts for the next time period. The Advance/Reset Signal 32 also causes the Address Counter 34 to sequence, through an 8 Bit Code Word, the Addressable Memory 38 to the next storage position such that when the next Read/Write Signal 36 occurs, the 8 Bit Code Word from the Event Counter 18 will be stored in the next sequentially available address position in the Memory 38. In this manner, the sums of all Activity Counts occurring between the Advance/Reset Signals 32 are stored in consecutive locations in the Addressable Memory 38.

When it is desirable to obtain the information stored in the Addressable Memory 38, the activity monitor is connected through appropriate electrical connections to a readout device which may be a computer or other device which can store the sequential information. Through appropriate inputs, such as EXTERNAL MEMORY CYCLE ENABLE, WRITE INHIBIT and RESET to the Control Logic Block 30, the memory is sequentially addressed and the data outputted to be recorded. When all the information has been removed from the Addressable Memory, the WRITE INHIBIT signal is terminated and all addresses in the memory are recycled resetting each memory address to zero. The RESET signal is then activated which resets the address counter 34 and timer 20 to zero. Thus, it is from the time of this RESET signal that the standard timing interval and the single count interval signals (STI 24 and SCI 26, respectively) are measured.

Figure 2:
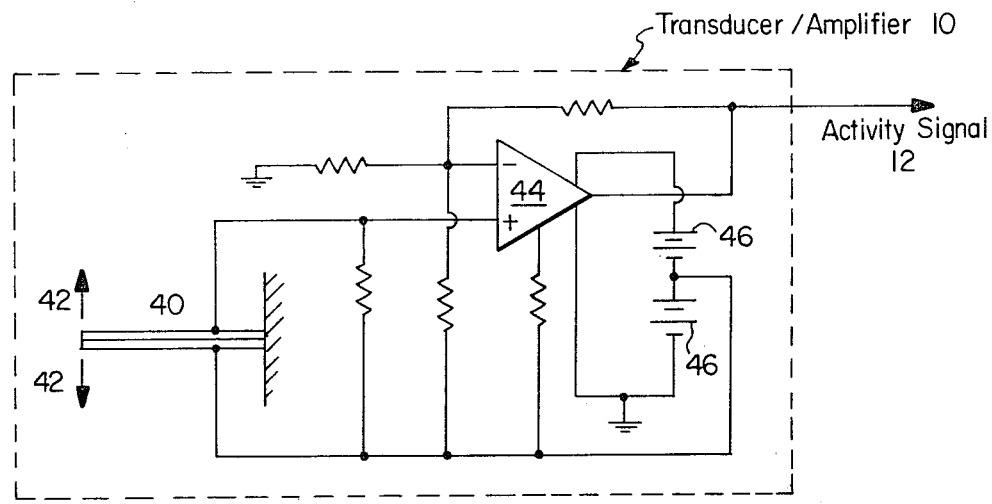
FIG. 2 is a diagramatical schematic of the transducer/amplifier block in FIG. 1.

Further understanding of the Transducer/Amplifier 10 will be facilitated by reference to FIG. 2. A transducer element 40 in one embodiment is comprised of a piezoelectric bilaminar bender element in a cantilever mounting. One end of the Element 40 is fixably mounted in the activity monitor case 11 with the other end free. A voltage is developed which is proportional to the mechanical deflection of the free end in the direction of the Arrows 42. Voltages developed in the transducer 40 are conveyed to a conventionally wired operational amplifier 44. The power for the amplifier and the activity monitor in general is supplied by batteries 46. When the transducer is accelerated by limb motion, it produces a voltage which is then amplified by the operational amplifier by a factor of 1000. The strength of the Activity Signal 12, which is outputted from the Transducer/Amplifier 10, is directly proportional to the deflection of transducer 40 due to movement of the subject's limb.

An Activity Count Limiter 14 may be utilized to control the total number of Activity Counts 16 which are inputted into the Event Counter 18. This is advantageous in the event that the gain of the Transducer/Amplifier 10 is set very high such that the slightest movement of the subject produces an Activity Count 16. A low damped oscillation in transducer 40 would provide a large number of activity counts for one movement before the signal strength had decayed to the point at which the Event Counter 18 would not be triggered. This high volume of counts could completely fill the limited number of counts available in Event Counter 18 such that data could overflow and reset the total number in Event Counter 18 to 0. As it would be impossible upon reading the data out of the activity monitor to determine whether a finite number of pulses in a time period was the first, second or third number of times the event counter set itself back to zero in a Standard Timing Interval, it is necessary to limit the inputs to the event counter.

The Activity Count Limiter 14 could consist of a monostable multivibrator which produces a single fixed time duration pulse output upon receiving an input which is above a threshold level. By appropriately setting the duration of the output pulse, it can be seen that the total number of pulses supplied to the event counter will not exceed its storageability regardless of the number of Activity Signals 12 forwarded from the Transducer/Amplifier 10.

In one embodiment, where the Event Counter 18 can store and provide an output Code Word for 4096 pulses, the duration of the output pulse monostable multivibrator would be the Standard Timing Interval divided by number of events which are countable by the Event Counter 18. If in one embodiment the Standard Time Interval is fifteen (15) minutes (900 seconds) and the Event Counter has a maximum count of 4096, then a pulse width of 0.22 seconds from the one-shot multivibrator would ensure that the data read out of the Event Counter would be accurate. As is well known, once an input triggers a one-shot multivibrator, subsequent inputs will not produce an output until a fixed duration of time has elapsed (the pulse width of the one-shot output). Thus, in this instance, additional Activity Signals 12 (whether caused by excessively high gain in the operational amplifier, undamped ringing of the transducer or in response to an exceptionally violent movement of the subject) would produce no further Activity Counts 16 to the Event Counter. Therefore, when the data is reviewed and there exists 4096 counts in a particular Standard Timing Interval, the researcher can be sure that in each 0.22 second Single Count Interval (SCI) a physical activity occurred which was above the threshold level for the Transducer/Amplifier 10 and Activity Count Limiter 14 system.

One-shot multivibrators have known instabilities which make them susceptible to temperature and humidity changes. In the human environment, it is not always possible to maintain the multivibrator at a uniformly standard temperature and pressure. Consequently, it is possible that the durational output of the multivibrator will vary and, thus, may pick up and register activity counts when it should not and vice versa. In a further preferred embodiment in the present application, the Activity Count Limiter 14 comprises a dual J-K flip-flop to implement the non-retriggerable delay function previously performed by the one-shot. During the Single Count Interval (SCI) the circuit is receptive to the Activity Signal 12 from the Transducer/Amplifier 10. If the Activity Signal 12 exceeds the preset threshold level during the SCI, an Activity Count 16 is generated at the end of the interval. It will be seen that only one threshold crossing is needed during the SCI to produce a pulse; and additional crossings during the interval have no effect, because only one pulse per SCI is produced.

Figure 3:
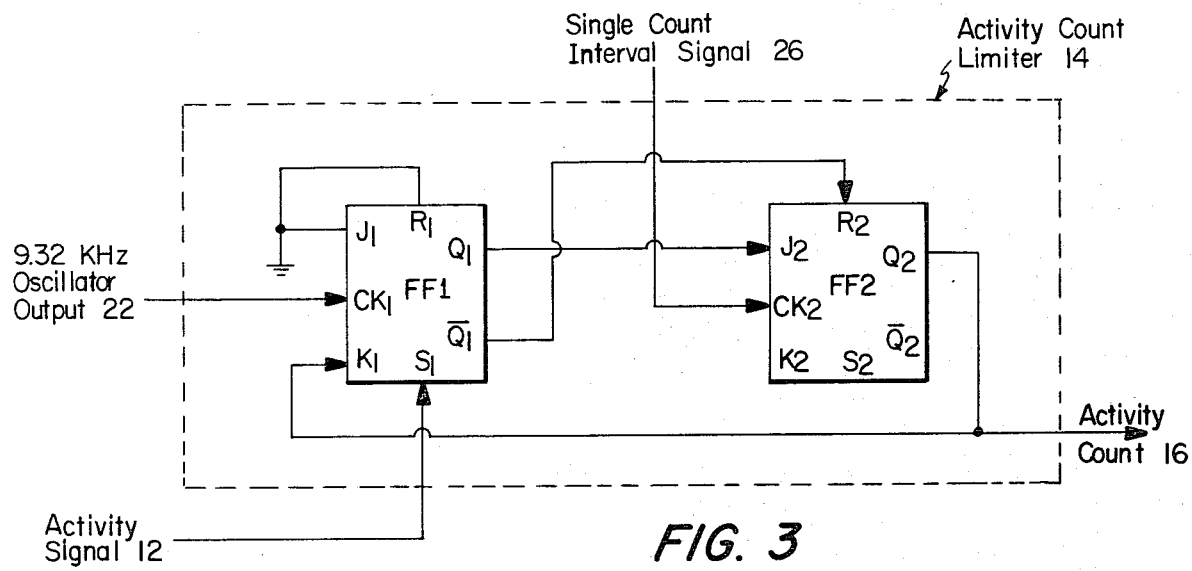
FIG. 3 is an electrical schematic of an embodiment of the activity count limiter in FIG. 1.
Figure 7:
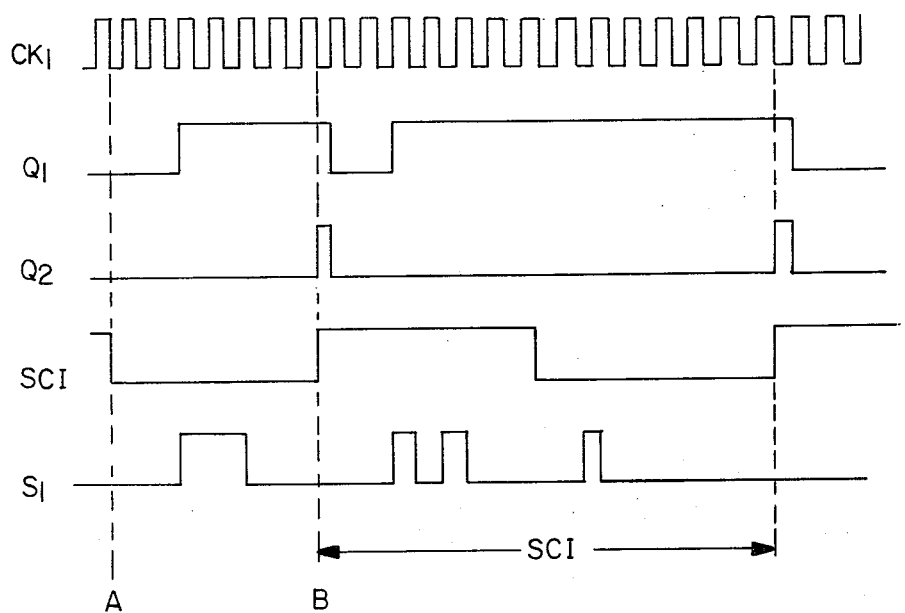
FIG. 7 is a sequence comparison of signals inputted to and outputted from the embodiment of the activity count limiter in FIG. 3.

Referring now to FIG. 3, each of the J-K flip-flops, for purposes of clarification, will be referred to as $FF_1$ and $FF_2$. The Oscillator Output 22 from Timer 20 is inputted at terminal $CK_1$ in $FF_1$. During the beginning (prior to receipt of an Activity Signal 12 above the threshold level) $Q_1$ will be at a low voltage (a logical 0) as shown in FIG. 7 at Point A. Therefore, $Q_2$ remains low also. When an Activity Signal 12, greater than the threshold level, is placed on $S_1$, $Q_1$ is immediately set to the high state (logical 1) and $\overline{Q}_1$ is reset to a low output (logical 0).

The setting of $\overline{Q}_1$ to 0 releases the reset ($R_2$) of $FF_2$. No further circuit action occurs until the low-to-high transition of the Single Count Interval (SCI) which is inputted to $CK_2$ in $FF_2$. This transition clocks $FF_2$ and $Q_2$ goes high. With $Q_2$ high, $K_1$ is enabled so that on the next low-to-high transition of the Oscillator Output 22, $Q_1$ is reset to its original low condition. With $Q_1$ reset, $\overline{Q}_1$ and $R_2$ resets $Q_2$ and, thus, a pulse, whose width is equal to one half the oscillator frequency's period, is generated. Thus, one Activity Count 16 is provided.

In the event that a number of pulses are received during the Single Count Interval, the dual flip-flops remain the same after the first pulse has caused $Q_1$ to go high. $Q_1$ remains high (and, thus, $Q_2$ is low) until the end of the Single Count Interval (when the SCI undertakes a low-to-high transition). At this point, a single output is provided at $Q_2$ and the dual flip-flops are reset for the next Single Count Interval.

In summary, regardless of the frequency of Activity Signal 12, the Activity Counts 16 will be separated from one another by a time no less than the Single Count Interval (SCI). Thus, by judicious choice of the Single Count Interval, it is possible to ensure that the Event Counter 18 will not be overloaded and, thus, all data will be accurate. In a particular embodiment, a 12-Bit Event Counter is utilized such that at most it can receive $2^{12}$ (4096) counts during any Standard Timing Interval (STI). Thus, to ensure against overload, the Single Count Interval will be equal to the STI divided by 4096. In one embodiment where the STI is equal to fifteen (15) minutes (900 seconds) then the Single Count Interval is equal to 0.22 seconds. In order to match the 12 Bit Counter to an 8 Bit Addressable Memory, only the 8 most significant Bits of the Event Counter are transmitted to the Addressable Memory with the 4 least significant Bits disregarded. However, it is equally clear that with a 12 Bit Memory (assuming size and space limitations permitted) it could easily accommodate all 12 Bits of the Event Counter Code. Similarly, by varying the size of the Event Counter and/or the Standard Timing Interval (STI), any Single Count Interval which is desirable could be provided. Thus, the activity monitor can be adjusted to varying levels of transducer sensitivity, activity signal frequency, signal timing interval, etc. depending upon the needs of the particular researcher.

Figure 4:
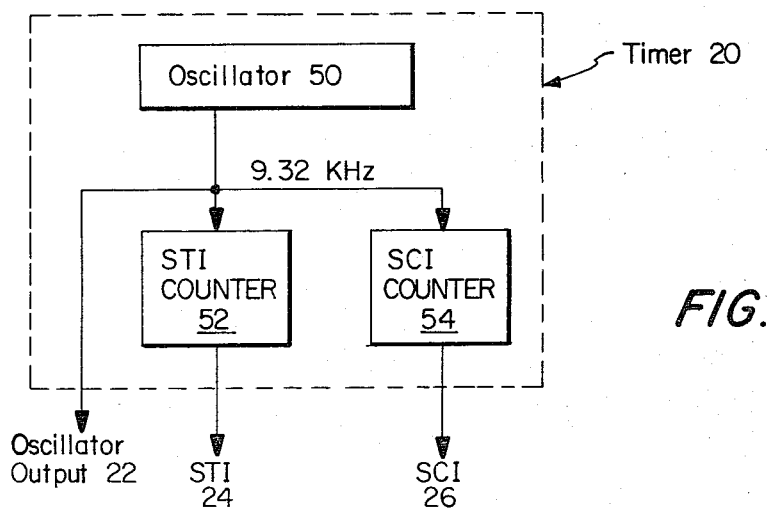
FIG. 4 is a block diagram of the timer block in FIG. 1.

Details of one embodiment of the Timer 20 are shown in FIG. 4. A conventional Oscillator 50 provides an Oscillator Output 22 which comprises a high frequency clock pulse. In a preferred embodiment the Oscillator is crystal controlled and provides an output of 18.641 KHz which is divided to produce an Oscillator Output of 9.32 KHz. Additionally, the Oscillator Output is fed into Counter Stages 52 and 54 to provide STI and SCI outputs, respectively. By suitable selection of the Counters 52 and 54, the Standard Timing Interval and the Single Count Interval can be adjusted to meet the needs of the subject and/or researcher. In a preferred embodiment a 24 Stage Counter is utilized which provides a variety of outputs which can easily be changed to vary the Standard Timing Interval from 1.875 minutes to 15 minutes. Additionally, a 14 Stage Counter is used to provide a Single Count Interval (SCI) of from 0.03 seconds to 0.22 seconds which is compatible with the variety of Standard Timing Intervals available in view of the 4096 counts that are available in a preferred embodiment of Event Counter 18. Changes in the storage capacity of the Event Counter and the Oscillator frequency would change the number of stages required in Counters 52 and 54 and they would be chosen accordingly.

The Control Logic 30 is provided to sequence the storage of code words from the Event Counter 18 into the Addressable Memory 30 and to sequence the Address Counter 34 in choosing storage spots in the Addressable Memory. However, it is also utilized by the EXTERNAL MEMORY CYCLE ENABLE and WRITE INHIBIT inputs when data is read out of the activity monitor.

Figure 5:
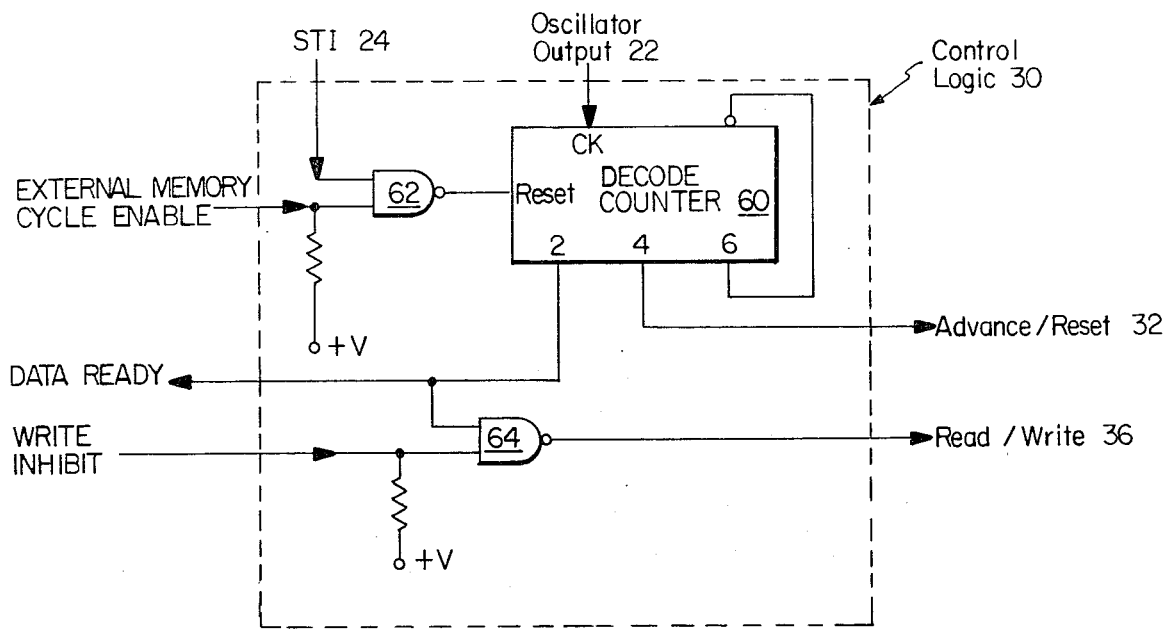
FIG. 5 is an electrical schematic depicting an embodiment of the control logic block in FIG. 1.

FIG. 5 is illustrative of a preferred embodiment of Control Logic 30. During data gathering and storage operations, there will be no input applied to the EXTERNAL MEMORY CYCLE ENABLE or WRITE INHIBIT input terminals and, thus, the only inputs are the Standard Timing Interval and the Oscillator Output. A Decade Counter has as its input Oscillator Output 22 (on the CK Input) and the output of NAND Gate 62. Thus, the Decade Counter 60 is reset by NAND Gate 62 by the negative transition of Standard Timing Interval 24 (or a negative transition pulse from the EXTERNAL MEMORY CYCLE ENABLE). Immediately after resetting, the Decade Counter 60 begins to count pulses from the Oscillator Output 22 such that pulses appear sequentially in order at Decade Counter outputs 2, 4 and 6.

When the pulse appears on the "2" decoded line, the input to NAND Gate 64 provides a Read/Write output 36 enabling the contents of Event Counter 18 to be recorded into the Addressable Memory 38 at the address determined by Address Counter 34. The appearance of a pulse on the "2" decoded line is also transmitted out of the activity monitor to the interface device and the reading computer signaling that the next data word in the memory is ready for reading (see FIG. 6 and the appropriate portion of the Specification). Two cycles of the Clock Pulse after the appearance of a pulse at line "2", a pulse appears at line "4". The "4" pulse appears as Advance/Reset 32 which is utilized to reset the Event Counter 18 and advance the Address Counter 34. The delay of two clock pulses ensures that the material from the Event Counter 18 has sufficient time to be read into the Addressable Memory 38 prior to the Event Counter's being reset to zero. Similarly, it ensures that the 8 Bit Code Word from the Event Counter 18 is read into the correct address in the Addressable Memory 38 as determined by the Address Counter 34 before advancing the Address Counter to the next sequential address.

Two clock pulses after the appearance of a pulse on the "4" line, a pulse appears on the "6" line which disables the Decade Counter, so that no further pulses are accepted by the Counter until the RESET line is again pulsed. As noted earlier, the RESET is pulsed once each Standard Timing Interval (STI) or each time there is an input on the EXTERNAL MEMORY CYCLE ENABLE terminal.

When data is being read out of the activity monitor, the appearance of a low level on the WRITE INHIBIT line prevents writing of information in the Addressable Memory 38 by the output along Read/Write 36. A high pulse is applied to the RESET input to the activity monitor (as seen in FIG. 1) setting the Address Counter at the first storage address. A low pulse is applied to the EXTERNAL MEMORY CYCLE ENABLE line initiating the counting procedure of the Decade Counter 60. When a pulse appears at line "2", DATA READY output goes to a high level indicating to the computer/monitor interface that the DATA OUT lines are ready to be sampled. The appearance of a subsequent pulse at line "4" advances the Address Counter to the next address and the system awaits the EXTERNAL MEMORY CYCLE ENABLE input from the reading computer. After all data has been read out, the memory can then be cleared by repeating the whole process with the WRITE INHIBIT line released. This causes the contents of the Event Counter, which is 0 because it is reset on every memory cycle, to be written in each memory address location.

Obviously, in view of the above teachings, there are many computers and interface devices which can adequately perform the reading and storage of data in Addressable Memory 38. The data could be read out and stored on magnetic tape, magnetic flexible disks or in a hard copy produced by a printer-plotter. Any computer with digital input and output lines can be used or a separate stand-alone readout device which stores the information in its own memory could be used to interrogate Addressable Memory 38.

Figure 6:
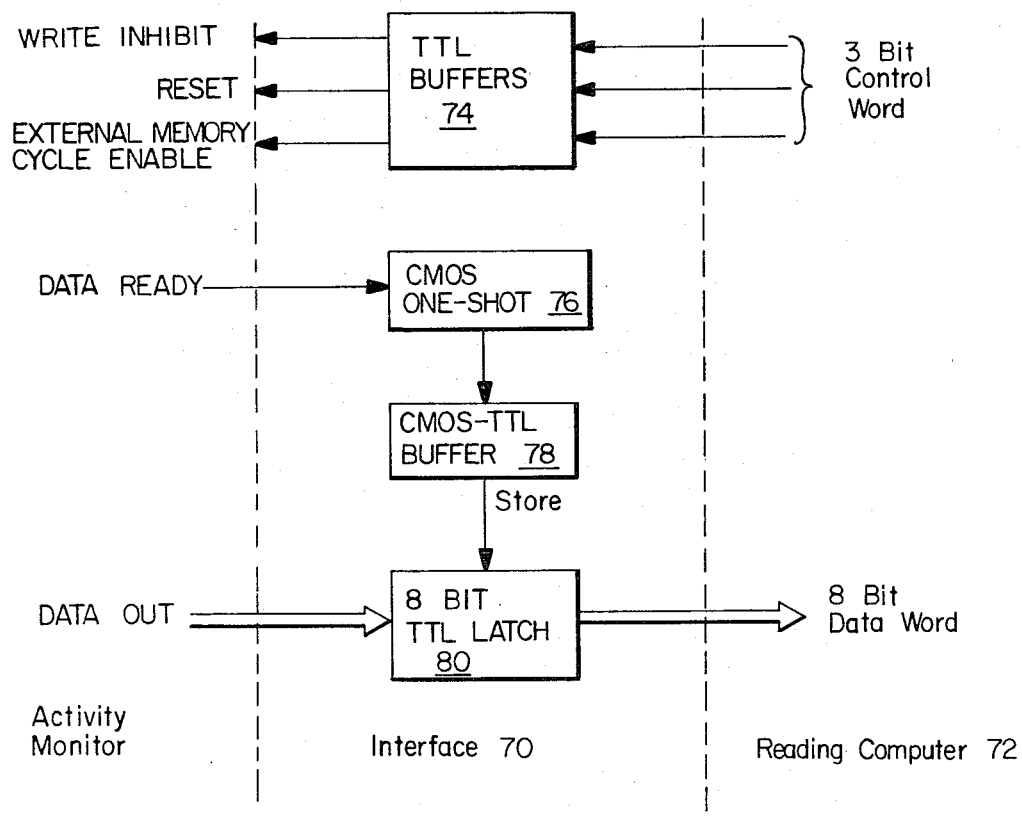
FIG. 6 is a logic schematic indicative of the interface between the activity monitor in FIG. 1 and a reading computer into which activity information is to be read.

FIG. 6 serves to illustrate one embodiment of Interface 70 between Reading Computer 72 and the activity monitor inputs and outputs. The computer would have as an output a 3 Bit Control Word that would be applied to Transistor-Transistor Logic (TTL) Buffers 74. These provide the WRITE INHIBIT, RESET, and EXTERNAL MEMORY CYCLE ENABLE signals which are inputted into the activity monitor. The DATA READY signal output of Control Logic 30 is supplied to Complementary Metal-Oxide Semiconductor (CMOS) One-Shot 76 which then provides a fixed duration output to the CMOS-TTL Buffer 78. The output from CMOS-TTL Buffer 78 causes 8 Bit TTL Latch 80 to store the 8 Bit Code Word from the activity monitor and pass it into the Reading Computer 72. In this embodiment, the CMOS One-Shot and the CMOS-to-TTL Buffer are necessitated by the logic circuitry utilized, although it is clear that in view of these teachings, many other possibilities and expediencies will become obvious to those of ordinary skill in the art.

Different research studies will have varying requirements on sensitivity, dynamic range, and Standard Timing Interval of the monitor. For example, sleep studies may require very high sensitivity to detect subtle movements, but a smaller dynamic range since the number of counts occurring in a standard timing period may be small. In studies on hyperactive children, however, the sensitivity could be lower, but the dynamic range may need to be much larger. Suitable choice of storage capacity in Event Counter 18 and Addressable Memory 38 will facilitate the total amount of time over which data can be stored before the device must be read out. In a preferred embodiment, a 256 word memory system provides a total time of 64 hours (256 times 15 minutes). It is noted that if the Addressable Memory 38 is completely filled and data is continued to be inputted into it, the Address Counter will reset itself and impress new data on the Addressable Memory 38 erasing the previous data. Therefore, the Addressable Memory 38 will retain the most recent 256 words representing activity levels. Obviously, by ensuring readout prior to overlap or increasing the size of the Addressable Memory 38, it is possible to ensure recovery of all data words.

Sensitivity may be varied in four ways in the activity monitor. The length of the transducer itself can be varied or different transducers can be utilized providing a variable electrical output for a given vibrational input. The gain and bias level of the operational amplifier can be varied to provide a higher or lower signal to the Activity Count Limiter. Varying the duration of the output pulse (in the case that a monostable multivibrator is utilized as the Activity Count Limiter 14) will tend to discriminate against rapid, repetitive and vibratory types of movements. Changes in the length of transducer, gain and bias level of the amplifier all tend to affect the minimum amplitude of acceleration which is detected, thus, discriminating against low acceleration and subtle movements.

In accordance with the above teachings, other activity monitors different from the embodiment described herein are possible. The detailed description of a specific embodiment set forth above is by way of illustration only and is not taken as limiting the scope of the invention.

What is claimed as new and desired to be secured by Letters Patent of the United States:

1. A self-contained single unit physiological monitoring system for monitoring physiological responses, said system comprising:
   transducer means for converting each physiological response to an electrical pulse output;
   timer/control means for providing standard timing interval signals;
   memory means electrically connected to said timer/control means and said transducer means, for recording a number of said pulse outputs over a standard timing interval and for storing said number of pulse outputs over more than one standard timing interval; and
   case means, mountable on a subject, for mounting said transducer means, said timer/control means, and said memory means.

2. A physiological monitoring system according to claim 1 wherein said transducer means comprises:
   transducer/amplifier means for providing an electrical signal in response to the monitored physiological response; and
   count limiting means, responsive to said transducer/amplifier means, for providing a fixed pulse output when said electrical signal exceeds a predetermined threshold level.

3. A physiological monitoring system according to claim 2 wherein said timer/control means further provides a single count interval signal and said count limiting means, in response to said single count interval signal, provides a maximum of one pulse output for each single count interval signal.

4. A physiological monitoring system according to claim 1 wherein said memory means comprises:

event counter means, responsive to said transducer means pulse output, for summing pulse outputs over said standard timing interval and providing an output representative of said sum;

addressable memory means, responsive to said event counter means output, for storing at an address said output representative of a sum of pulse outputs during a standard timing interval; and addressing means, responsive to said standard timing interval signal, for sequentially shifting the address in said addressable memory means wherein said sum of pulse outputs for a standard timing signal is stored.

5. A physiological monitoring system according to claim 1 wherein said timer/control means comprises:
timer means for providing standard timing interval signals; and
control means, responsive to said timer means and external commands, for providing standard time intervals to said memory means and for controlling readout of said memory means.

6. An activity monitor for recording periodic activity levels of a subject, said monitor comprising:
timer means for providing an oscillator output, a standard timing interval signal, and a single count interval signal;
transducer/amplifier means for providing an electrical signal in response to the subject activity;
count limiting means, responsive to said transducer/amplifier means, for providing a fixed pulse output when said electrical signal exceeds a predetermined threshold level;
event counter means, responsive to said pulse output, for summing pulse outputs during a standard timing interval and providing an output representative of said sum;
addressable memory means, responsive to said even counter means output, for storing at an address said output representative of a sum of pulse outputs during a standard timing interval; and
addressing means, responsive to said standard timing interval signal, for sequentially shifting the address in said addressable memory means wherein said sum of pulse outputs for a standard timing signal is stored.

7. An activity monitor for recording periodic activity levels of a subject according to claim 6 wherein said addressable memory means includes external readout means for providing an output indicative of the sum of pulses at a specified address in said memory means.

8. An activity monitor for recording periodic activity levels of a subject according to claim 7 wherein said activity monitor further comprises a control means for selectively addressing said memory means in response to an external input and for activating said external readout means.

9. An activity monitor for recording periodic activity levels of a subject according to claim 8 wherein said transducer/amplifier means comprises:
piezoelectric means for providing an electrical output in response to movement of the means; and
amplifier means for amplifying the piezoelectric means output.

10. An activity monitor for recording periodic activity levels of a subject according to claim 9 where said count limiting means comprises a monostable multivibrator for providing a fixed duration output pulse in response to the output of said amplifier means exceeding a predetermined threshold level.

11. An activity monitor for recording periodic activity levels of a subject according to claim 9 wherein said count limiting means comprises:
dual J-K flip-flop means, responsive to said single count interval signal and said oscillator output, for providing a single output pulse if and only if said amplifier means output exceeds said threshold level at least once during said single count interval.

12. An activity monitor for recording periodic activity levels of a subject according to claim 11 wherein said timer means comprises:
oscillator means for producing an oscillator output;
counter means, responsive to said oscillator output, for counting pulses in said oscillator output and for providing a standard timing interval signal and a single count interval signal.

13. A self-contained method of monitoring physiological responses on a subject comprising the steps of:
measuring said physiological response on said subject;
providing on said subject an electrical output indicative of said measured physiological response;
providing a fixed pulse output if said electrical output exceeds a predetermined threshold value;
summing on said subject the fixed pulse outputs over a predetermined time period; and
automatically recording on said subject the sum of fixed pulse outputs for a plurality of said predetermined time periods.

14. The method of claim 13 wherein said step of measuring said physiological response includes the step of measuring the activity level of a human subject.

15. A method of recording periodic activity levels of an ambulatory subject on said subject without limiting mobility of said subject, said method comprising the steps of:
providing on said subject a standard timing interval signal;
providing on said subject an electrical signal in response to activity of said subject;
providing on said subject a fixed pulse output when said electrical signal exceeds a predetermined threshold level;
summing on said subject said pulse outputs during a standard timing interval defined by said standard timing interval signal and providing an output representative of said sum;
automatically storing on said subject at an addressable location said output representative of a sum of pulse outputs during a standard timing interval; and
sequentially shifting said addressable location after each standard timing signal such that a plurality of outputs representative of a sum of pulse outputs during a standard timing interval can be stored.

16. Apparatus for monitoring physiological motor activity comprising a miniaturized capsule adapted to be affixed to and worn by the person being monitored, said capsule containing:
(a) a motion sensing means sensitive to linear and rotational movements of said capsule,
(b) electronic scaling means in circuit with said motion sensing means for providing an output of pulses corresponding in number to units of motor activity, each unit of which comprises a predetermined plurality of said movements, as registered by said motion sensing means, (c) an integrated electronic accumulator connected to said scaling means for accumulating said output of pulses from said scaling means, (d) multi-cell random-access-memory means connected to said accumulator, and (e) a quartz crystal oscillator and a frequency divider means cooperatively functioning to provide timing pulses at timed intervals to said accumulator whereby to effect the delivery repetitively by said accumulator of the output of pulses relating to the number of units of activity accumulated thereon during the immdiately preceding timed interval to said memory means.

17. Apparatus for monitoring physiological motor activity, according to claim 16, wherein said apparatus further comprises electronic addressing counter means for directing the data as to number of units of activity to successive cells of said memory means.

18. Apparatus for monitoring physiological motor activity, according to claim 17 wherein said apparatus additionally comprises means for transferring data from said memory means to an external permanent storage means.

19. A self-contained single unit physiological monitoring system for monitoring physiological events, said system comprising:

transducer means for converting each physiological event to an electrical pulse output;

timer means for providing standard timing interval signals;

accumulator means connected to said transducer means for accumulating a number corresponding to said pulse outputs in one standard timing interval;

memory means connected to said accumulator means for receiving and storing a series of said numbers corresponding to said pulse outputs from a series of said standard timing intervals;

control means connected to said timer means, said accumulator means, and said memory means for directing successive numbers corresponding to said pulse outputs to successive locations in said memory means; and case means, mountable on a subject, for mounting said transducer means, said timer means, said accumulator means, said memory means, and said control means.

20. A self-contained single unit physiological monitoring system for monitoring physiological events, said system comprising:

transducer means for converting each physiological event to an electrical pulse output;

timer means for providing standard timing interval signals;

accumulator means connected to said transducer means for accumulating a number corresponding to said pulse outputs in one standard timing interval;

memory means connected to said accumulator means for receiving and storing a first number corresponding to said pulse outputs at the end of a first standard timing interval and then a subsequent number corresponding to said pulse outputs at the end of a subsequent timing interval;

control means connected to said timer means, accumulator means, and said memory means for directing said first number corresponding to said pulse outputs to a first location in said memory means and directing said subsequent number corresponding to said pulse outputs to a subsequent location in said memory means; and case means, mountable on a subject, for mounting said transducer means, said timer means, said accumulator means, and said control means.

* * * * *